(12) United States Patent
Romanowski et al.

(10) Patent No.: US 11,969,262 B2
(45) Date of Patent: Apr. 30, 2024

(54) PROXIMAL CONNECTOR FOR GUIDEWIRE ASSEMBLY

(71) Applicant: St. Jude Medical International Holding S.à r.l., Luxembourg (DE)

(72) Inventors: Jason Romanowski, Bloomington, MN (US); Amanuel Seretse, New Brighton, MN (US); Rajnish Panday, Savage, MN (US)

(73) Assignee: St. Jude Medical International Holding S.a.r.l., Luxembourg (DE)

( * ) Notice: Subject to any disclaimer, the term of this patent is extended or adjusted under 35 U.S.C. 154(b) by 587 days.

(21) Appl. No.: 17/122,610

(22) Filed: Dec. 15, 2020

(65) Prior Publication Data
US 2021/0137459 A1 May 13, 2021

Related U.S. Application Data

(63) Continuation of application No. 15/637,293, filed on Jun. 29, 2017, now abandoned.
(Continued)

(51) Int. Cl.
*A61B 5/00* (2006.01)
*A61B 5/01* (2006.01)
(Continued)

(52) U.S. Cl.
CPC .............. *A61B 5/6851* (2013.01); *A61B 5/01* (2013.01); *A61B 5/026* (2013.01); *A61B 5/036* (2013.01);
(Continued)

(58) Field of Classification Search
CPC . A61B 2562/12; A61B 2562/227; A61B 5/01; A61B 5/0215; A61B 5/026;
(Continued)

(56) References Cited

U.S. PATENT DOCUMENTS

| 5,938,624 A | 8/1999 | Akerfeldt et al. |
| 6,090,052 A | 7/2000 | Akerfeldt et al. |

(Continued)

FOREIGN PATENT DOCUMENTS

| EP | 1849409 A1 | 10/2007 |
| WO | 9843318 A1 | 10/1998 |

(Continued)

OTHER PUBLICATIONS

International Search Report and Written Opinion for International Patent Application No. PCT/US2019/028482, dated Jul. 25, 2019, 15 pages.
(Continued)

*Primary Examiner* — Scott Luan
(74) *Attorney, Agent, or Firm* — Armstrong Teasdale LLP (57) ABSTRACT

The present disclosure provides an improved guidewire assembly including a sensor disposed on a distal portion thereof and a proximal connector disposed on a proximal portion thereof for electrically coupling the guidewire assembly to an external device. The proximal connector comprises at least one proximal contact and at least one reflowed insulative element disposed adjacent the at least one proximal contact.

20 Claims, 8 Drawing Sheets

Related U.S. Application Data (60) Provisional application No. 62/356,761, filed on Jun. 30, 2016.

(51) Int. Cl.
*A61B 5/026* (2006.01)
*A61B 5/03* (2006.01)
*A61B 5/06* (2006.01)
*A61M 25/09* (2006.01)
*A61B 5/0215* (2006.01)

(52) U.S. Cl.
CPC .............. *A61B 5/062* (2013.01); *A61M 25/09* (2013.01); *A61B 5/0215* (2013.01); *A61B 2562/12* (2013.01); *A61B 2562/227* (2013.01); *A61M 2025/09083* (2013.01); *A61M 2025/09091* (2013.01); *A61M 2025/09108* (2013.01); *A61M 2025/09133* (2013.01)

(58) Field of Classification Search
CPC ......... A61B 5/036; A61B 5/062; A61B 5/685; A61M 2025/09083; A61M 2025/09091; A61M 2025/09108; A61M 2025/09133; A61M 25/09
See application file for complete search history.

(56) References Cited

U.S. PATENT DOCUMENTS

| | | | |
|---|---|---|---|
| 2010/0137928 A1* | 6/2010 | Duncan .................... | A61N 1/05 439/669 |
| 2012/0245457 A1* | 9/2012 | Crowley .............. | A61B 8/4477 600/424 |
| 2014/0068936 A1* | 3/2014 | Finley .................. | A61N 1/0551 29/877 |
| 2016/0064862 A1 | 3/2016 | Nagasaki et al. | |
| 2017/0014562 A1 | 1/2017 | Liebing et al. | |

FOREIGN PATENT DOCUMENTS

| | | |
|---|---|---|
| WO | 2013033426 A2 | 3/2013 |
| WO | 2015113044 A1 | 7/2015 |

OTHER PUBLICATIONS

Lathiya ("Polyolefin Heat Shrink Tubing for Tight-Tolerance Medical Applications," 2011).

\* cited by examiner

PROXIMAL CONNECTOR FOR GUIDEWIRE ASSEMBLY

CROSS-REFERENCE TO RELATED APPLICATIONS

This application is a continuation of U.S. patent application Ser. No. 15/637,293, filed Jun. 29, 2017, which claims the benefit of priority to U.S. Provisional Patent Application No. 62/356,761, filed Jun. 30, 2016, both of which are hereby incorporated herein by reference in their entirety.

BACKGROUND OF THE INVENTION

A. Field of the Invention

The present disclosure relates generally to a guidewire assembly including a proximal portion configured for electrical connection to an external device. In particular, the present disclosure relates to a guidewire assembly having a proximal connector disposed on a proximal portion thereof, the proximal connector including at least one electrical contact and at least one reflowed insulative segment bonded or sealed to an adjacent electrical contact.

B. Background

Various diagnostic and therapeutic procedures in or on the body of a patient, such as in the circulatory system, the gastrointestinal tract, the brain vessels, the bronchial tree or the like, may be performed or facilitated by inserting a catheter into a body lumen and thereafter navigating the diagnostic or therapeutic catheter to the target site prior to, for example, delivering a medical device to the target site. To facilitate navigation of the catheter or other medical device, a guidewire is often used. The guidewire typically has a reduced diameter relative to the catheter or device; the reduced diameter aids a physician in inserting and navigating the guidewire to the target site. The catheter or device is then passed over the guidewire and guided to the target site.

One method of maneuvering a guidewire to a target site within a patient is to place one or more position sensors on the guidewire, track the position sensors with a navigation system, and display a real-time or rendered image of the guidewire for the clinician manipulating the guidewire to view. Further, in many medical procedures, it may be desirable to monitor and/or analyze various physiological parameters within the body of a patient through a physiological data sensor. The raw signal generated by the position sensor and/or physiological data sensor located within the body may be transmitted to an external device, in which the raw signal is re-translated into locational or physiological data. The re-translated longitudinal or physiological data is then processed and the results continuously displayed on a monitor and/or saved.

In order to power the position and/or physiological data sensor and/or to communicate signals generated by the sensor(s), some known guidewires utilize one or more cables or leads extending along an internal portion of the guidewire between the sensor and a proximal connector. Some known guidewires utilize a physical electrical connection between the proximal connector and an external device to transfer power or communicate generated signals thereto, while other known guidewires utilize a wireless connection between the proximal connector and the external device. To transfer power or generated signals to or from the proximal connector, the proximal connector includes at least one electrically isolated area for the connection to be made. The isolated area(s) are generally bonded or sealed to an insulative element so as to prevent liquid or moisture from entering the internal portion of the guidewire, contacting internal electrical components, and causing an electrical short.

BRIEF SUMMARY OF THE INVENTION

The present disclosure is directed to a guidewire assembly comprising: a guidewire having a distal portion and a proximal portion; a sensor disposed at the distal portion of the guidewire; and a proximal connector disposed at the proximal portion of the guidewire. The proximal connector comprises at least one proximal contact and at least one reflowed insulative element disposed adjacent the at least one proximal contact.

The present disclosure is further directed to a guidewire comprising: a distal portion comprising a sensor; a shaft portion coupled to the distal portion; and a proximal connector coupled to the shaft portion. The proximal connector comprises at least one proximal contact and at least one reflowed insulative element disposed adjacent the at least one proximal contact.

The present disclosure is further directed to a guidewire assembly obtained by a process comprising: forming a proximal connector, the proximal connector comprising a first proximal contact and a first insulative element disposed adjacent a distal end of the first proximal contact; distally advancing a heat shrink tube over the proximal connector; heating the heat shrink tube and the proximal connector to reflow the first insulative element so as to couple the first insulative element to the distal end of the first proximal contact; and removing the heat shrink tube from the proximal connector.

The foregoing and other aspects, features, details, utilities, and advantages of the present disclosure will be apparent from reading the following description and claims, and from reviewing the accompanying drawings.

DETAILED DESCRIPTION

Many medical devices, including catheters or other devices, are delivered to a target site within a patient via a guidewire assembly that includes a sensor at a distal end thereof for determining the relative position of the guidewire assembly within the patient or for relaying data relative to certain physiological parameters of the patient, such as temperature, pressure, or rate of fluid (e.g. blood) flow. To provide an electrical connection between the sensor and an external device, such as a display or monitoring device, the guidewire assembly may include a proximal connector at the proximal end thereof that includes at least one electrical contact and at least one insulative segment electrically isolating the electrical contact from the remainder of the guidewire assembly and from any other electrical contacts included in the proximal connector. Because contact between internal electrical components of the guidewire assembly and fluid or moisture should be avoided, it is generally desirable that the isolated electrical contact(s) and the insulative segment(s) adjacent thereto are sealed or bonded to one another in order to prevent such fluid or moisture contact with the internal electrical components from occurring. Further, it is also generally desirable to provide a guidewire assembly having sufficient rigidity to aid in delivery of the catheter or other medical device and having a substantially uniform longitudinal or concentric alignment between the electrical contact(s) and the insulative segment(s).

Thus, it is desirable to provide a guidewire assembly including a sensor at a distal end thereof and a proximal connector at a proximal end thereof, wherein the proximal connector is rigid, is substantially longitudinally or concentrically aligned along a length thereof, and is sealed to prevent fluid or moisture from contacting the internal electrical components of the guidewire assembly. It is also desirable to provide methods or processes of making and using such guidewire assemblies. The present disclosure is directed to a guidewire assembly, and the process of making and using the guidewire assembly, that provides a proximal connector that is rigid, longitudinally and concentrically aligned, and sealed so as to prevent fluid or moisture from contacting internal electrical components of the guidewire assembly.

The guidewire assemblies described herein are designed for use with a wide variety of catheters or other medical devices and implants. In one embodiment of the present disclosure, the guidewire assembly includes a sensor at a distal end thereof and a proximal connector at a proximal end thereof for electrically connecting the sensor to an external device, such as a display or monitoring device. The proximal connector includes at least one electrical contact (or proximal contact) and an insulative element positioned adjacent to the electrical contact. The material forming the insulative element is capable of being reflowed during production of the guidewire assembly so as to create a bond or seal (preferably a hermetic seal) with the adjacent electrical contact. By utilizing a reflowable material, such as nylon, to form the insulative segment, an electrical contact and adjacent insulative element are securely bonded together while also creating a seal or barrier between external fluid or moisture and internal electrical components. Further, use of a reflowable material as the insulative elements in forming the proximal connector, as compared to other conventional methods of forming a proximal connector, provides an improved longitudinal or concentric alignment along a length of the proximal connector as well as the desired rigidity of the proximal portion of the guidewire assembly. The method of making a proximal connector for use in a guidewire assembly, as described in more detail below, also provides a streamlined and more efficient method of manufacturing the proximal connector as compared to other conventional methods of manufacturing a proximal connector known in the art.

Figure 1:
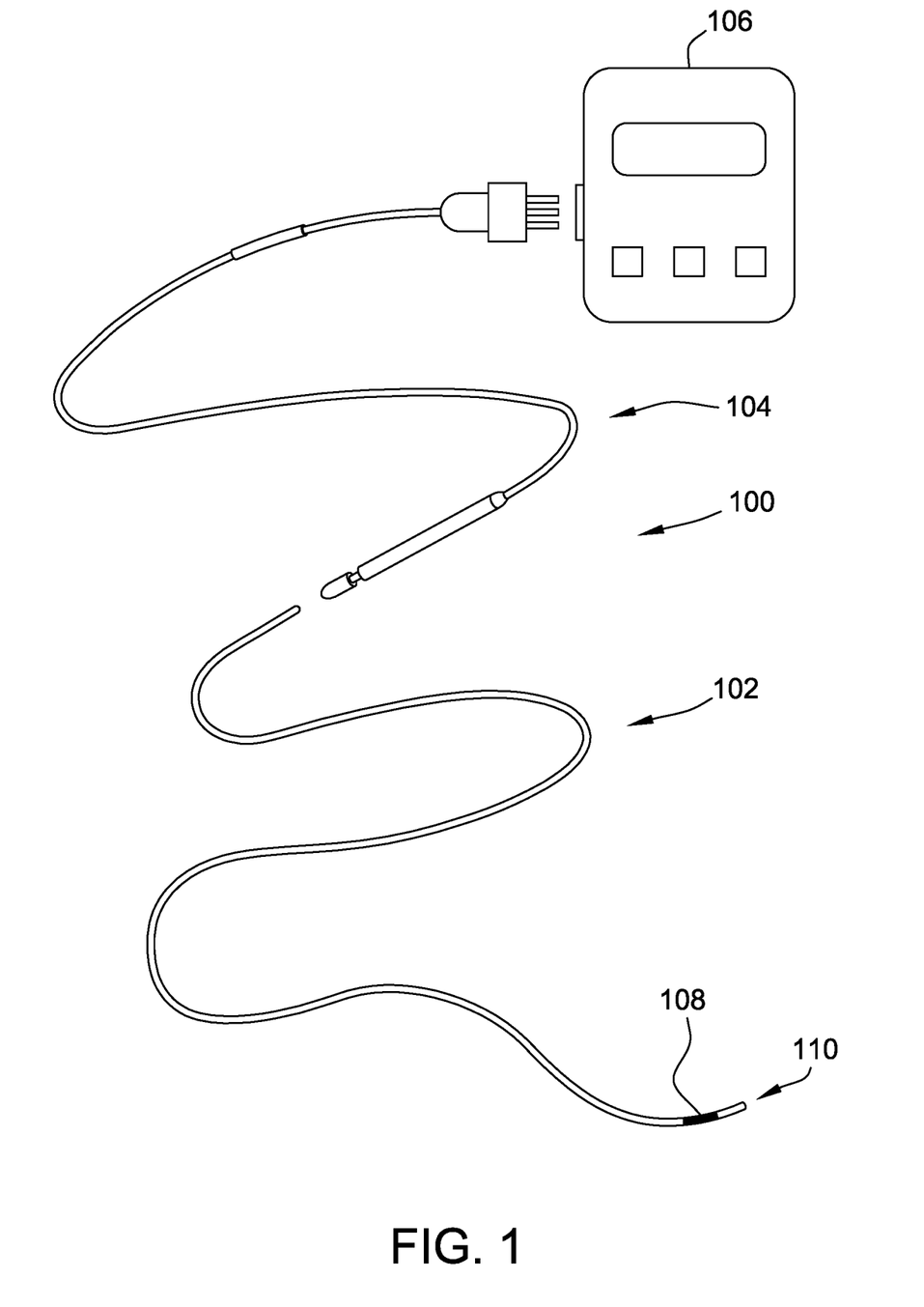
FIG. 1 is a diagrammatic view of a conventional system for performing one or more diagnostic or therapeutic procedures utilizing a guidewire assembly.

Referring now to the Figures, FIG. 1 illustrates one exemplary embodiment of a conventional system 100 for performing one or more diagnostic or therapeutic procedures utilizing a guidewire assembly 102.

Among other components, system 100 includes a guidewire assembly 102, an interface cable 104 capable of being coupled to and electrically communicating with guidewire assembly 102, and an external device 106, such as a signal processor, computer, or other control unit, capable of being coupled to and electrically communicating with interface cable 104. Guidewire assembly 102 includes a sensor 108, such as a positional sensor or a physiological data sensor, positioned on a distal portion 110 of guidewire assembly 102. Sensor 108 is configured to electrically communicate with interface cable 104 and thus external device 106. That is, external device 106, interface cable 104, and guidewire assembly 102 are configured such that signals generated by sensor 108 are transmitted through guidewire assembly 102, to interface cable 104, and to external device 106 so as to communicate information obtained by sensor 108, such as location, position, or physiological data, to a user. External device 106 may include, for example and without limitation, an electronic control unit (ECU), a display device, a user input device, memory, and the like. It should be understood that system 100 may further include other conventional components such as, for example and without limitation, additional sensors, catheters, medical devices, coupling or connecting means, and the like. Further, it should be understood that system 100 may utilize wireless transmission of a signal generated by sensor 108 to external device 106, such as via a transmitter or transceiver unit (not shown) adapted to wirelessly communicate via a radio frequency signal with a communication unit (not shown) arranged in connection with external device 106.

Figure 2:
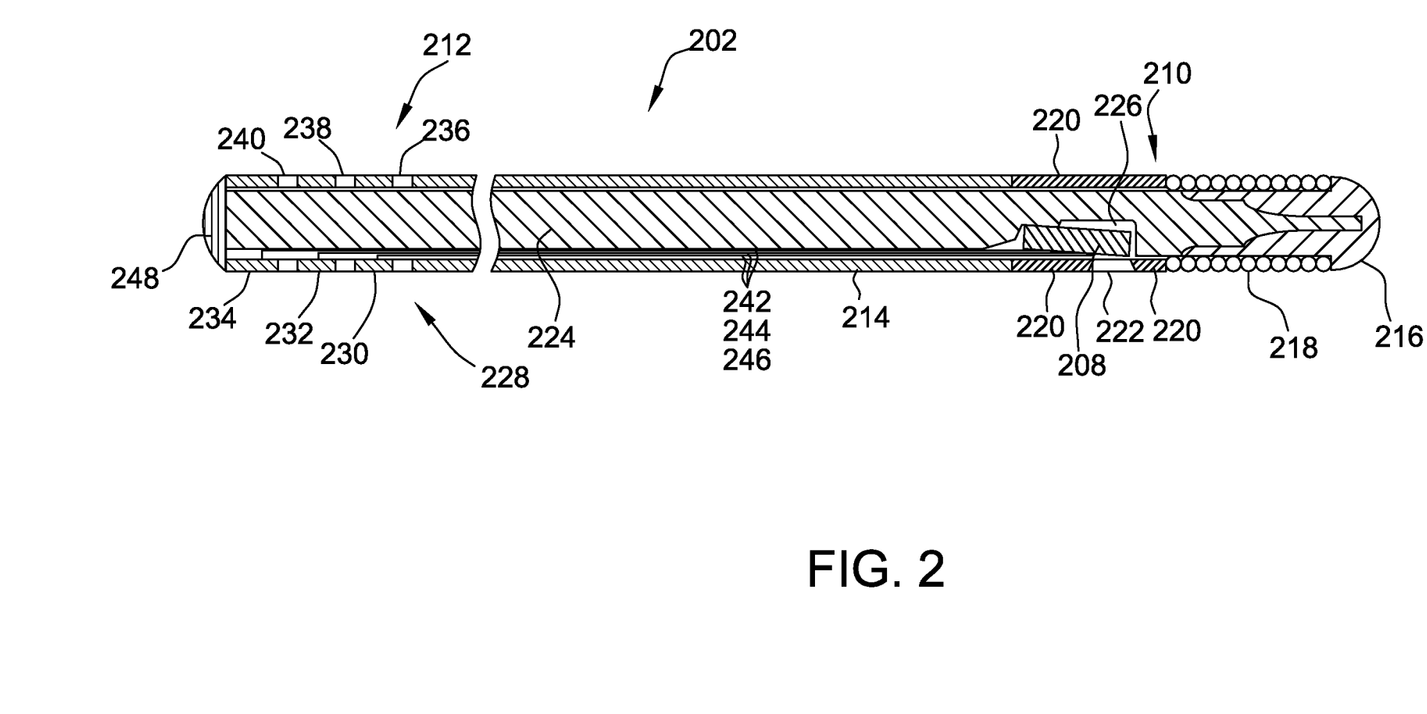
FIG. 2 is a cross-sectional view of one embodiment of a guidewire assembly of the present disclosure.
Figure 3:
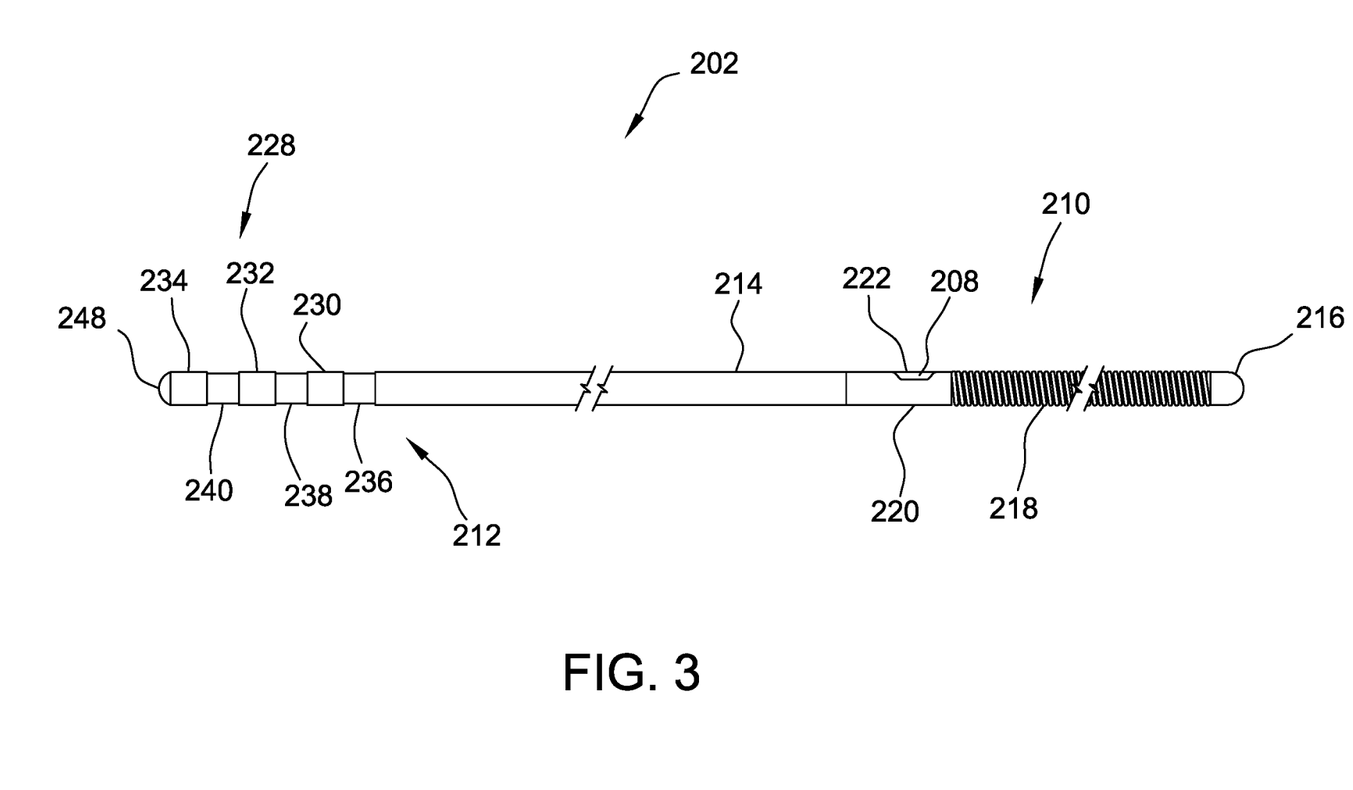
FIG. 3 is a perspective view of the guidewire assembly of FIG. 2.

FIG. 2 is a cross-sectional view of a guidewire assembly of the present disclosure, and FIG. 3 is a perspective view of the guidewire assembly of FIG. 2. Guidewire assembly 202 includes a distal portion 210, a proximal portion 212, and a flexible sheath 214 extending therebetween. In this particular embodiment, distal portion 210 includes a distal tip 216 coupled to a distal end of a distal spring coil 218, and an outer jacket 220 which is coupled at a distal end thereof to a proximal end of distal spring coil 218. Outer jacket 220 serves as a housing for a sensor 208 and includes a window or opening 222 through which sensor 208 is exposed to the outer portion of guidewire assembly 202 and thus the medium, e.g. blood, surrounding guidewire assembly 202 when introduced into a patient. Sensor 208 may include any sensor known in the art and suitable for use within a guidewire assembly during a therapeutic or diagnostic procedure, such as and without limitation, a pressure sensor, a temperature sensor, a rate of fluid (e.g. blood) flow sensor, and or a positioning or location sensor. Flexible sheath 214 is coupled at a distal end thereof to a proximal end of outer jacket 220 and may comprise a single tubular member as shown in FIGS. 2 and 3 or may comprise two, or three, or more flexible components coupled to one another. Further, flexible sheath 214 may be in the form of a tubular member as shown in FIGS. 2 and 3 or may be in the form of a coil spring (not shown). A core wire 224 (not shown in FIG. 3) extends from proximal portion 212 through distal portion 210 and into distal tip 216. Core wire 224 includes a recess 226 in which sensor 208 is disposed. Flexible sheath 214 and core wire 224 may be comprised of any material known in the art suitable for use in a guidewire assembly.

Proximal portion 212 of guidewire assembly 202 includes proximal connector 228 configured to communicate with an external device, such as external device 106 shown in FIG. 1. Proximal connector 228, as illustrated in FIGS. 2 and 3, includes a first proximal contact 230, a second proximal contact 232, and a third proximal contact 234, each of which are annular or tubular components, such as a ring electrode, longitudinally aligned with one another along core wire 224. First, second, and third proximal contacts 230, 232, and 234 are electrically insulated from one another and from the remainder of guidewire assembly 202 by first insulative element 236, second insulative element 238, and third insulative element 240, each of which are annular or tubular elements longitudinally aligned with one another as well as with first, second, and third proximal contacts 230, 232, and 234. In particular, first insulative element 236 is positioned distal to and adjacent first proximal contact 230, second insulative element 238 is positioned distal to and adjacent second proximal contact 232, and third insulative element 240 is positioned distal to and adjacent third proximal contact 234. That is, first, second, and third proximal contacts 230, 232, and 234 are positioned in an alternating relationship with first, second, and third insulative elements 236, 238, and 240. It should be understood by one skilled in the art that proximal connector 228 may include one, two, four, five or more proximal contacts and/or insulative elements without departing from the scope of the present disclosure so long as the proximal contacts and insulative elements are arranged in an alternating configuration such that each proximal contact is insulated from one another and from the remainder of guidewire assemble 202 by at least one insulative element.

A first transmitting cable 242, a second transmitting cable 244, and a third transmitting cable 246 (not shown in FIG. 3) extend from first, second, and third proximal contacts 230, 232, and 234, respectively, to sensor 208 so as to electrically couple first, second, and third proximal contacts 230, 232, and 234 for transmission of a signal generated by sensor 208 or for transmission of power to sensor 208. Proximal connector 228 further includes an atraumatic proximal tip 248 coupled to a proximal end of third proximal contact 234 that closes or otherwise seals a proximal end of guidewire assembly 202. In one embodiment, proximal tip 248, for example and without limitation, comprises an adhesive. In other embodiments, proximal tip 248 may comprise an epoxy, metal, or other material known in the art suitable for use in a guidewire assembly.

In one embodiment, first, second, and third proximal contacts 230, 232, and 234 may be comprised of, for example and without limitation, a gold plated stainless steel tubing. In other embodiments, for example and without limitation, first, second and third proximal contacts 230, 232, and 234 may be comprised of platinum, gold, copper, or other electrically conductive materials as would be known to one of skill in the art.

First, second, and third insulative elements 236, 238, and 240 may be comprised of any material that may be reflowed so as to create a bond or seal (preferably a hermetic seal) with an adjacent proximal contact to prevent or minimize fluid or moisture from contacting internal electrical components of guidewire assembly 202. In one particular embodiment, first, second, and third insulative elements 236, 238, and 240 may comprise a reflowable thermoplastic material, such as nylon or polyester block amides. In one embodiment, first, second, and third insulative elements 236, 238, and 240 may be coated with a hydrophobic material, such as polytetrafluoroethylene (PTFE) or fluorinated ethylene propylene (FEP). A suitable process for forming a bond or seal between adjacent proximal contacts and insulative elements is discussed in more detail below.

Figure 4:
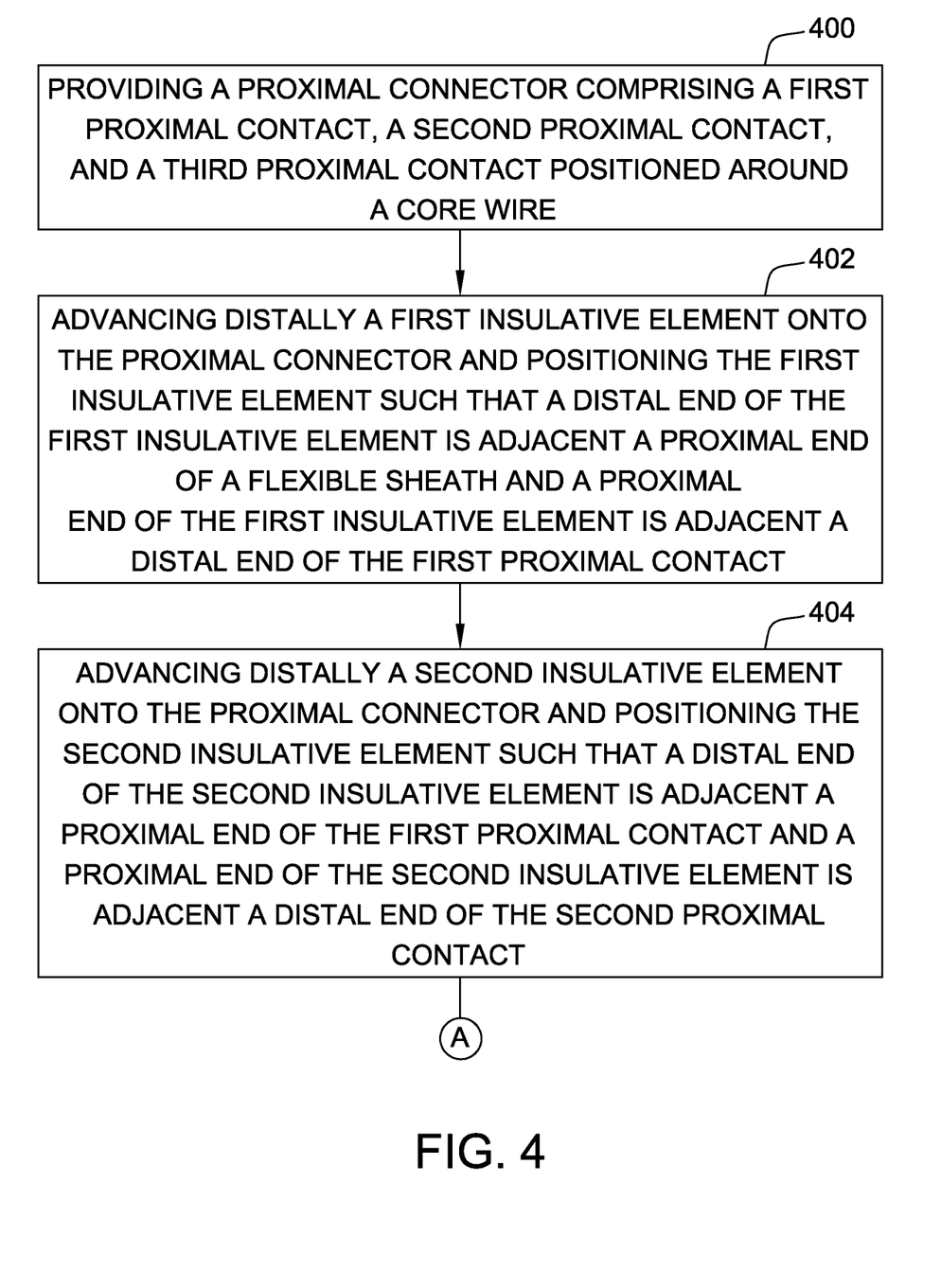
FIGS. 4, 4A, and 4B are a flowchart of one embodiment of a method of making a proximal connector for use in the guidewire assembly of FIGS. 2 and 3.
Figure 4A:
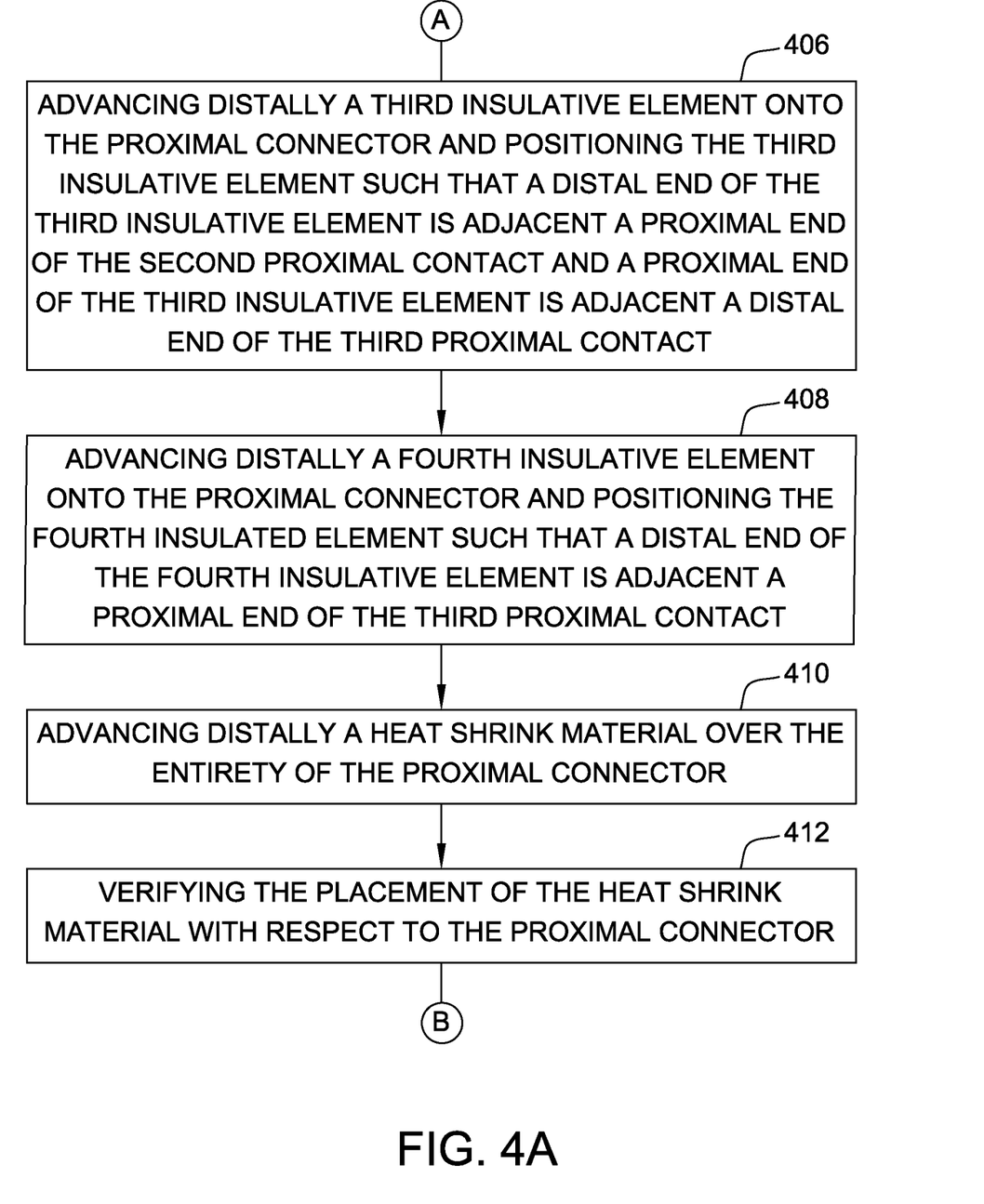
Figure 4B:
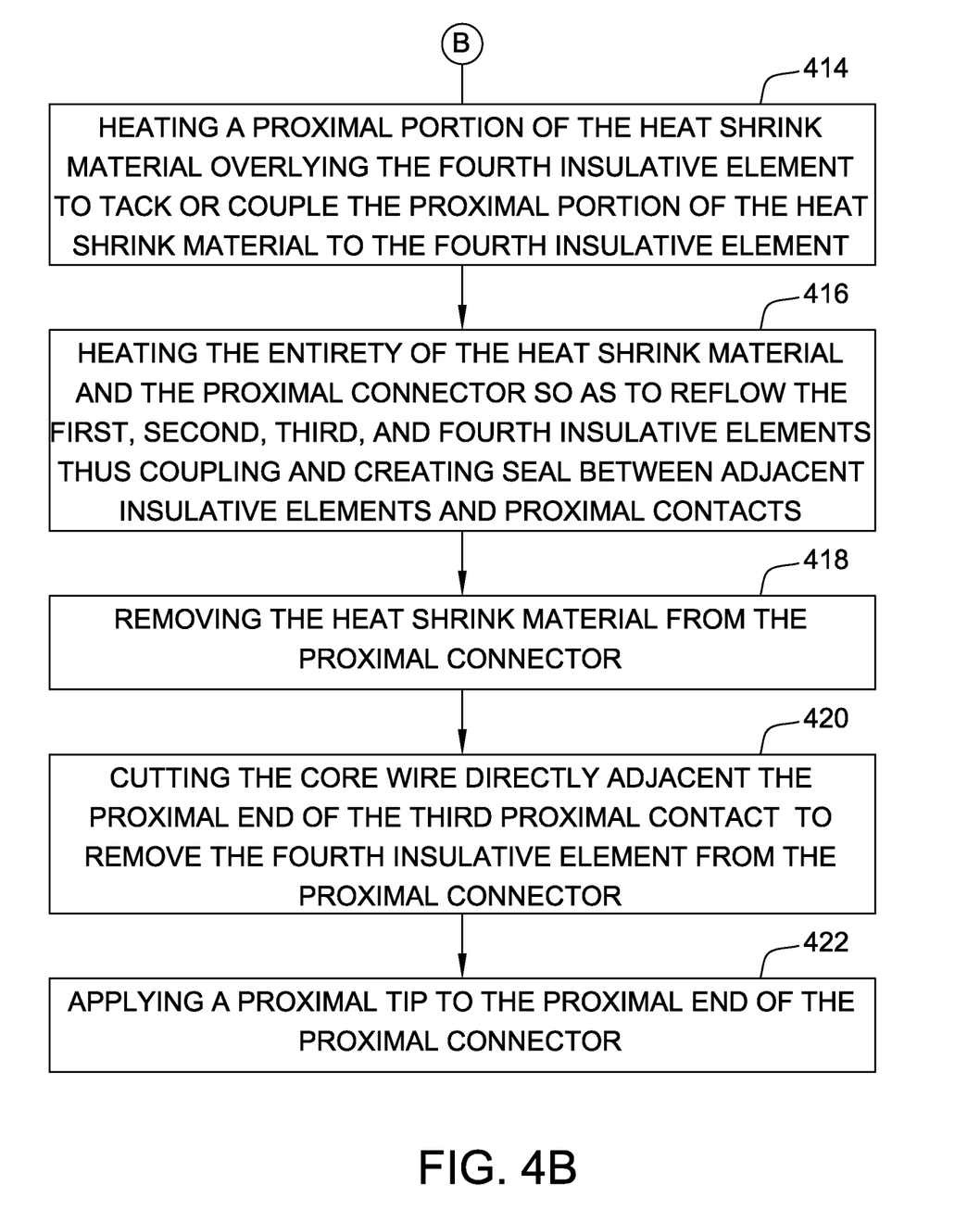
Figure 5A:
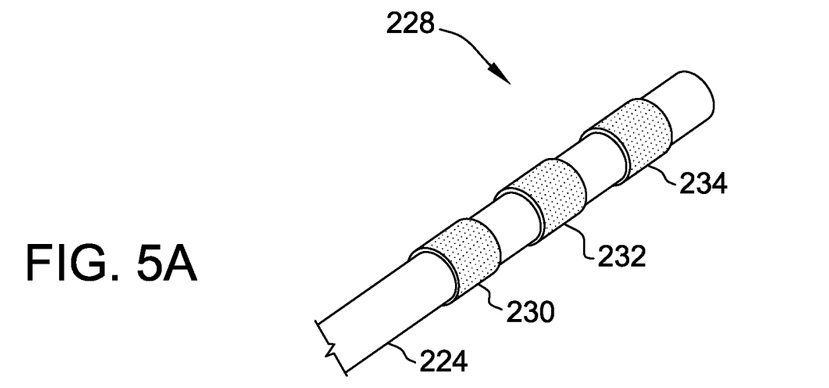
FIGS. 5A-5E are perspective views of the proximal connector at various stages of the method illustrated in FIGS. 4, 4A, and 4B.
Figure 5B:
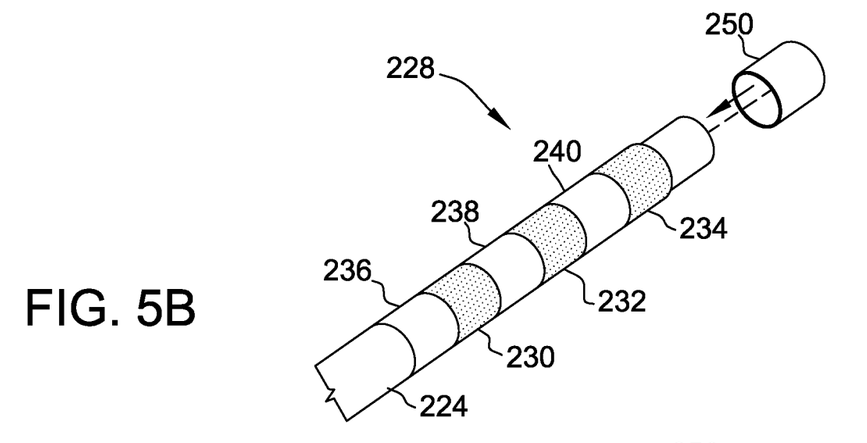

In accordance with various embodiments of the present disclosure, guidewire assembly 202, as shown in FIGS. 2 and 3, may be manufactured utilizing any number of suitable manufacturing techniques that can produce the desired structure. In one embodiment, as illustrated in FIG. 4, proximal connector 228 of guidewire assembly 202 is manufactured by first providing 400 proximal connector 228 comprising first proximal contact 230, second proximal contact 232, and third proximal contact 234 positioned around core wire 224 as shown in FIG. 5A and as described above in detail. First, second, and third proximal contacts 230, 232, and 234 may be positioned on and coupled to core wire 224 (also referred to as a chamfered wire) by any suitable method known to those skilled in the art. First insulative element 236 is then advanced distally 402 onto proximal connector 228 and positioned such that a distal end of first insulative element 236 is adjacent a proximal end of flexible sheath 214 (not shown in FIGS. 5A-5E) and a proximal end of first insulative element 236 is adjacent a distal end of first proximal contact 230, as shown in FIG. 5B. Similarly, second insulative element 238 is advanced distally 404 onto proximal connector 228 and positioned such that a distal end of second insulative element 238 is adjacent a proximal end of first proximal contact 230 and a proximal end of second insulative element 238 is adjacent a distal end of second proximal contact 232, as shown in FIG. 5B. Third insulative element 240 is then advanced distally onto proximal connector 228 and positioned such that a distal end of third insulative element 240 is adjacent a proximal end of second proximal contact 232 and a proximal end of third insulative element 240 is adjacent a distal end of third proximal contact 234, as shown in FIG. 5B. A fourth insulative element 250 is then advanced distally onto proximal connector 228 and positioned such that a distal end of fourth insulative element 250 is adjacent a proximal end of third proximal contact 234, as shown in FIG. 5B. As shown in FIG. 5B, each of the first, second, and third proximal contacts 230, 232, and 234 as well as each of the first, second, third, and fourth insulative elements 236, 238, 240, and 250 are generally longitudinally or concentrically aligned with one another. As noted above, first, second, third, and fourth insulative elements 236, 238, 240, and 250 are comprised of any material that may be reflowed, such as nylon.

One skilled in the art will appreciate, as noted above, that proximal connector 228 may comprise, in other embodiments of the present disclosure, one, two, four, five, or more proximal contacts. It will be further appreciated by one skilled in the art that in embodiments comprising other than three proximal contacts as described above with respect to FIG. 4, insulative elements should be positioned on proximal connector 228 in an alternating arrangement with respect to the proximal contacts such that an insulative element is present at least at the distal end of proximal connector 228, and in some embodiments also at the proximal end of proximal connector 228.

Figure 5C:
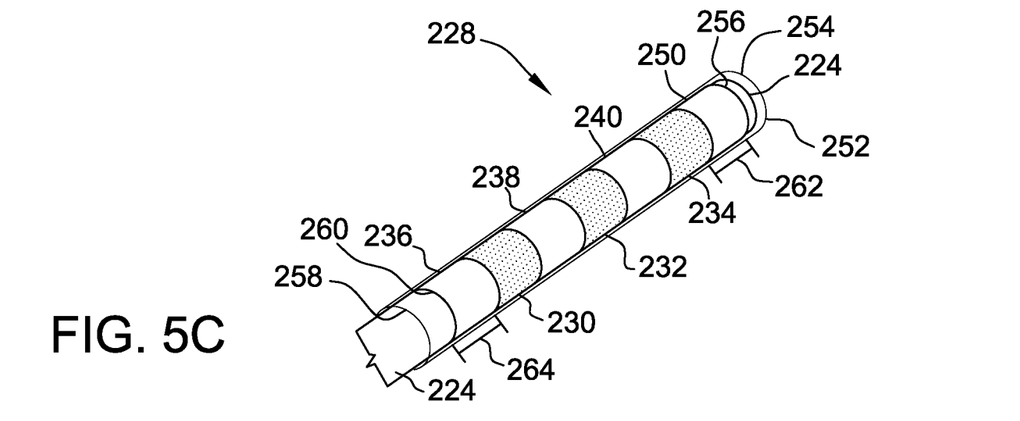

Once first, second, third, and fourth insulative elements 236, 238, 240, and 250 are positioned on proximal connector 228, a heat shrink material 252 is advanced distally 410 over proximal connector 228 such that heat shrink material 252 is positioned over an entirety of proximal connector 228 (i.e., a proximal end 254 of heat shrink material 252 extends past a proximal end 256 of proximal connector 228 and a distal end 258 of heat shrink 252 extends past a distal end 260 of proximal connector 228), as shown in FIG. 5C. Heat shrink material 252 is in the form of a hollow cylindrical tube and may be comprised of any suitable material known in the art suitable for use in a reflow process, such as polyethylene and fluorinated ethylene propylene (FEP). In one embodiment, proximal end 254 of heat shrink material 252 extends beyond proximal end 256 of proximal connector 228 by a minimum of 4 mm. In other embodiments, proximal end 254 of heat shrink material 252 extends beyond proximal end 256 of proximal connector 228 by about 4-10 mm. In yet other embodiments, proximal end 254 of heat shrink material 252 extends beyond proximal end 256 of proximal connector 228 by a minimum of 10 mm or more. In another embodiment, distal end 258 of heat shrink material 252 extends beyond distal end 260 of proximal connector 228 by a minimum of 4 mm. Once heat shrink material 252 is positioned over an entirety of proximal connector 228, the placement of heat shrink material 252 with respect to proximal connector 228 is verified 412.

After verifying 412 the placement of heat shrink material 252 with respect to proximal connector 228, a proximal portion 262 of heat shrink material 252 overlying fourth insulative element 250 is heated 414 so as to tack or couple proximal portion 262 of heat shrink material 252 to fourth insulative element 250. By heating proximal portion 262 of heat shrink material 252 over fourth insulative element 250, heat shrink material 252 may be held in place over proximal connector 228 so as to reduce movement of heat shrink material 252 with respect to proximal connector 228 during subsequent manufacturing of proximal connector 228. In another embodiment (not annotated in FIG. 4), a distal portion 264 of heat shrink material 252 overlying first insulative element 236 may be heated so as to tack or couple distal portion 264 of heat shrink material 252 to first insulative element 236. In one embodiment, for example and without limitation, heat shrink material 252 may be heated with a hot air pencil or hot air gun for a minimum of about 30 seconds at a temperature of from about 350 degrees Fahrenheit to about 400 degrees Fahrenheit.

Although described above as including the positioning of fourth insulative element 250 on proximal connector 228 during the making or forming of proximal connector 228, the step of positioning fourth insulative element 250 on proximal connector 228 may be omitted in an alternative embodiment. In this particular alternative embodiment, the step of heating 414 a proximal portion 262 of heat shrink material 252 overlying fourth insulative element 250 is also omitted.

The entirety of heat shrink material 252 and proximal connector 228 is then heated 416 so as to reflow first, second, third, and fourth insulative elements 236, 238, 240, and 250 thus coupling adjacent insulative elements and proximal contacts and creating a seal from external fluid and moisture therebetween. In one embodiment, for example and without limitation, heat shrink material 252 and proximal connector 228 are placed entirely within (and centered within) a hot air nozzle and heated for about 40 seconds to about 60 seconds at a temperature of from about 305 degrees Fahrenheit to about 325 degrees Fahrenheit.

Figure 5D:
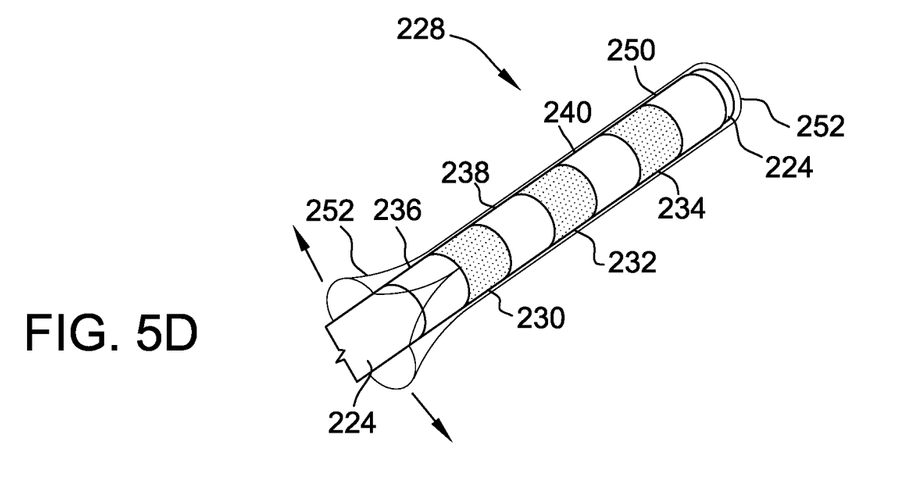
Figure 5E:
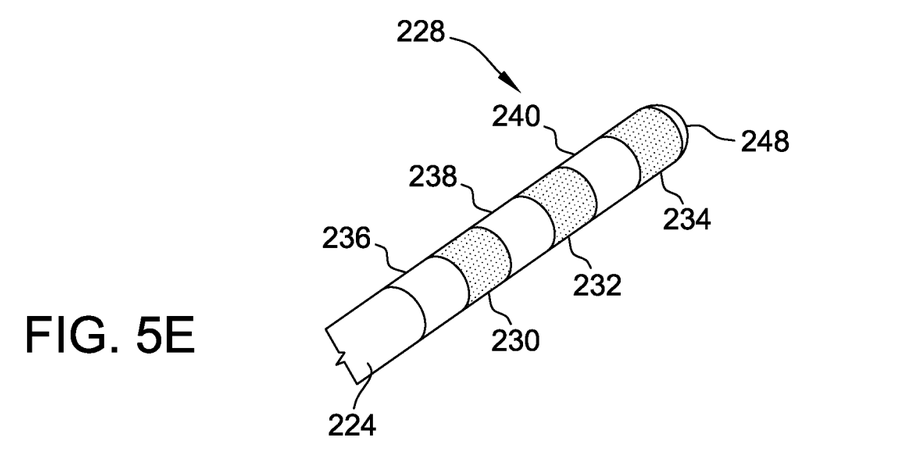

Heat shrink material 252 is then removed 418 from proximal connector 228, as shown in FIG. 5D. In one embodiment, heat shrink material 252 is removed with tweezers or other similar device, although it will be understood by one skilled in the art that heat shrink material 252 may be removed from proximal connector 228 by any suitable means known to those skilled in the art. Core wire 224 is then cut 420 directly adjacent the proximal end of third proximal contact 234 such that fourth insulative element 250 and any portion of core wire 224 extending proximally from the proximal end of third proximal contact 234 is removed from proximal connector 228. It will be understood by one skilled in the art that in embodiments comprising other than three proximal contacts, core wire 224 will be cut directly adjacent a proximal end of the most proximally positioned proximal contact of proximal connector 228.

Proximal tip 248 is then applied 422 to proximal end 256 of proximal connector 228. Applying proximal tip 248 may comprise applying an adhesive, epoxy, metal, or other material such that proximal tip 248 is suitable for use on a guidewire assembly (e.g., is atraumatic). In one particular embodiment, for example and without limitation, applying 422 proximal tip 248 to proximal connector 228 comprises applying a suitable glue or adhesive to a proximal end of core wire 224 and a proximal end of third proximal contact 234 and curing proximal tip 248 using, for example, a curing oven, solder tip, hot air, or other suitable method known to those skilled in the art for about 60 seconds at a temperature of about 140 degrees Celsius to about 160 degrees Celsius.

Although embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method for manufacturing a medical device assembly, the method comprising:
   providing an elongate body including a first ring electrode encircling the body, and a second ring electrode encircling the body;
   advancing a first, ring-shaped insulative element over the body until the first insulative element is positioned between the first ring electrode and the second ring electrode, is disposed adjacent a distal end of the first ring electrode, and is disposed adjacent a proximal end of the second ring electrode;

advancing a second, separate, ring-shaped insulative element over the body until the second insulative element is disposed adjacent a proximal end of the first ring electrode;

subsequent to advancing the first insulative element and advancing the second insulative element, advancing a heat shrink tube over the elongate body, the first insulative element, and the second insulative element;

heating only a portion of the heat shrink tube to couple that portion of the heat shrink tube to one of the first insulative element and the second insulative element and secure a position of the heat shrink tube relative to the elongate body and the first and second insulative elements; and subsequent to heating the portion of the heat shrink tube, heating an entirety of the heat shrink tube, wherein heating the entirety of the heat shrink tube:

reflows the first insulative element to couple the first insulative element to the distal end of the first ring electrode, to form a seal between the first insulative element and the distal end of the first ring electrode, to couple the first insulative element to the proximal end of the second ring electrode, and to form a seal between the first insulative element and the proximal end of the second ring electrode; and reflows the second insulative element to couple the second insulative element to the proximal end of the first ring electrode, and to form a seal between the second insulative element and the proximal end of the first ring electrode.

2. The method of claim 1, wherein the medical device assembly is a guidewire assembly.

3. The method of claim 1, wherein:
heating only a portion of the heat shrink tube comprises heating the portion of the heat shrink tube for at least 30 second at a temperature in a range from 350 degrees Fahrenheit to 400 degrees Fahrenheit; and
heating an entirety of the heat shrink tube comprises heating the entirety of the heat shrink tube for a time period in a range from 40 seconds to 60 seconds at a temperature in a range from 305 degrees Fahrenheit to 325 degrees Fahrenheit.

4. The method of claim 1, wherein the elongate body further includes a third ring electrode encircling the body.

5. The method of claim 4, further comprising:
advancing a third ring-shaped insulative element over the body until the third insulative element is disposed adjacent a distal end of the second ring electrode and adjacent a proximal end of the third ring electrode; and
reflowing, via the heating of the entirety of the heat shrink tube, the third insulative element to couple the third insulative element to the distal end of the second ring electrode, to form a seal between the third insulative element and the distal end of the second ring electrode, to couple the third insulative element to the proximal end of the third ring electrode, and to form a seal between the third insulative element and the proximal end of the third ring electrode.

6. The method of claim 1, further comprising coupling the first and second ring electrodes to an external device.

7. The method of claim 1, further comprising disposing a sensor at a distal end of the elongate body.

8. The method of claim 7, wherein the sensor is a pressure, temperature, and/or flow sensor.

9. The method of claim 7, wherein the sensor is a magnetic positioning sensor.

10. A method for manufacturing a medical device assembly, the method comprising:
forming a proximal connector, the proximal connector including an elongate body, a first proximal contact encircling the body, and a second proximal contact encircling the body;
advancing a first, ring-shaped insulative element over the body until the first insulative element is positioned between the first proximal contact and the second proximal contact, is disposed adjacent a distal end of the first proximal contact, and is disposed adjacent a proximal end of the second proximal contact;
advancing a second, separate, ring-shaped insulative element over the body until the second insulative element is disposed adjacent a proximal end of the first proximal contact;
subsequent to advancing the first insulative element and advancing the second insulative element, advancing a heat shrink tube over the elongate body, the first insulative element, and the second insulative element;
heating only a portion of the heat shrink tube to couple that portion of the heat shrink tube to one of the first insulative element and the second insulative element and secure a position of the heat shrink tube relative to the elongate body and the first and second insulative elements; and
subsequent to heating the portion of the heat shrink tube, heating an entirety of the heat shrink tube, wherein heating the entirety of the heat shrink tube:
reflows the first insulative element to couple the first insulative element to the distal end of the first proximal contact, to form a seal between the first insulative element and the distal end of the first proximal contact, to couple the first insulative element to the proximal end of the second proximal contact, and to form a seal between the first insulative element and the proximal end of the second proximal contact; and
reflows the second insulative element to couple the second insulative element to the proximal end of the first proximal contact, and to form a seal between the second insulative element and the proximal end of the first proximal contact.

11. The method of claim 10, wherein the medical device assembly is a guidewire assembly.

12. The method of claim 10, wherein:
heating only a portion of the heat shrink tube comprises heating the portion of the heat shrink tube using a hot air pencil or hot air gun; and
heating an entirety of the heat shrink tube comprises heating the entirety of the heat shrink tube using a hot air nozzle.

13. The method of claim 10, further comprising:
cutting the body adjacent the proximal end of the first proximal contact to remove a proximal portion of the body and the second insulative element.

14. The method of claim 13, further comprising attaching a tip to the proximal end of the first proximal contact.

15. The method of claim 10, wherein the proximal connector further includes a third proximal contact encircling the body.

16. The method of claim 15, further comprising:
advancing a third ring-shaped insulative element over the body until the third insulative element is disposed adjacent a distal end of the second proximal contact and adjacent a proximal end of the third proximal contact; and reflowing, via the heating of the entirety of the heat shrink tube, the third insulative element to couple the third insulative element to the distal end of the second proximal contact, to form a seal between the third insulative element and the distal end of the second proximal contact, to couple the third insulative element to the proximal end of the third proximal contact, and to form a seal between the third insulative element and the proximal end of the third proximal contact.

17. The method of claim 10, further comprising coupling the first and second proximal contacts to an external device.

18. The method of claim 10, further comprising disposing a sensor at a distal end of the elongate body.

19. The method of claim 18, wherein the sensor is a pressure, temperature, and/or flow sensor.

20. The method of claim 18, wherein the sensor is a magnetic positioning sensor.

\* \* \* \* \*